United States Patent [19]

Twardowski et al.

[11] Patent Number: 5,569,182
[45] Date of Patent: Oct. 29, 1996

[54] CLOT RESISTANT MULTIPLE LUMEN CATHETER AND METHOD

[75] Inventors: Zbylut J. Twardowski; W. Kirt Nichols; John C. Van Stone, all of Columbia, Mo.

[73] Assignee: The Curators of the University of Missouri, Columbia, Mo.

[21] Appl. No.: 386,473

[22] Filed: Feb. 9, 1995

Related U.S. Application Data

[63] Continuation-in-part of Ser. No. 45,016, Apr. 8, 1993, Pat. No. 5,405,320, which is a continuation-in-part of Ser. No. 772,613, Oct. 8, 1991, Pat. No. 5,209,723, which is a continuation of Ser. No. 461,684, Jan. 8, 1990, abandoned.

[51] Int. Cl.$^6$ .................................................. A61M 3/00
[52] U.S. Cl. .............................. 604/43; 604/49; 604/264
[58] Field of Search ............................ 604/93, 43–45, 604/280, 281, 282, 264

[56] References Cited

U.S. PATENT DOCUMENTS

| | | |
|---|---|---|
| D. 272,651 | 2/1984 | Mahurkar . |
| 3,612,038 | 10/1971 | Halligan . |
| 3,890,977 | 6/1975 | Wilson . |
| 3,935,857 | 2/1976 | Co . |
| 4,117,836 | 10/1978 | Erickson . |
| 4,134,402 | 1/1979 | Mahurkar . |
| 4,292,976 | 10/1981 | Banka . |
| 4,385,631 | 5/1983 | Uthmann . |
| 4,392,855 | 7/1983 | Oreopoulos et al. . |
| 4,405,313 | 9/1983 | Sisley et al. . |
| 4,531,933 | 7/1985 | Norton et al. . |
| 4,568,329 | 2/1986 | Mahurkar . |
| 4,581,012 | 4/1986 | Brown et al. . |
| 4,583,968 | 4/1986 | Mahurkar . |
| 4,681,564 | 7/1987 | Landreneau . |
| 4,681,570 | 7/1987 | Dalton . |
| 4,687,471 | 8/1987 | Twardowski et al. . |
| 4,692,141 | 9/1987 | Mahurkar . |
| 4,694,838 | 9/1987 | Wijayarthna et al. . |
| 4,701,159 | 10/1987 | Brown et al. . |
| 4,735,620 | 4/1988 | Ruiz . |
| 4,772,269 | 9/1988 | Twardowski et al. . |

(List continued on next page.)

FOREIGN PATENT DOCUMENTS 0132344   1/1985   European Pat. Off. .

OTHER PUBLICATIONS

Brochure by Quinton Instrument Co., 3.9mm Triple Lumen Catheter, 2 pages ©1988.
Brochure, Cath–tech, The Groshong Peripherally Inserted Central Venous Catheter ©1988.
Article by Twardowski et al. "Blood Recirculation in Intravenous Catheters for Hemodialysis"1,2, pp. 1978–1981, vol. 3, No. 12, 1993.
Article by Moss et al. "Use of a Silicon Catheter With a Dacron Cuff for Dialysis Short–Term Vascular Access" American Journal of Kidney Diseases, vol. XII, No. 6 (Dec.), 1988 pp. 492–498.
Article by Moss et al. "Use of a Silicon Dual–Lumen Catheter With a Long–Term Vascular Access for Hemodialysis Patients", Amer. Jour. of Kidney Diseases, vol. XVI, No. 3 (Sep.), 1990: pp. 211–215.
Brochure by Quinton Instrument Company entitled Instructions for Use Catheter Repair Kits –2 pages, Aug. 1993.

*Primary Examiner*—John D. Yasko
*Attorney, Agent, or Firm*—Gerstman, Ellis & McMillin, Ltd.

[57] ABSTRACT

Blood is circulated through a multiple lumen catheter which connects between a vein of a patient and the blood treatment device. The catheter and the lumens thereof each define distal ends which are positioned within the vein. By this invention, one withdraws blood from the vein through one of the lumens at a flow rate of at least about 200 ml./min. while also inserting blood into the vein through another of said lumens at a similar flow rate. The distal ends of the lumens are longitudinally spaced from each other by no more than about 5 mm. It have been found that the following advantages can be achieved by this method: less clot formation coupled with low direct blood recirculation and longer catheter survival. Also, the catheter works well in either direction of blood flow through the respective lumens.

10 Claims, 3 Drawing Sheets

U.S. PATENT DOCUMENTS

| | | |
|---|---|---|
| 4,790,809 | 12/1988 | Kuntz . |
| 4,808,155 | 2/1989 | Mahurkar . |
| 4,834,709 | 5/1989 | Banning et al. . |
| 4,846,814 | 7/1989 | Ruiz . |
| 4,867,742 | 9/1989 | Calderon . |
| 4,895,561 | 1/1990 | Mahurkar . |
| 4,935,004 | 6/1990 | Cruz . |
| 4,961,731 | 10/1990 | Bodicky et al. . |
| 4,981,477 | 1/1991 | Schon et al. . |
| 4,985,014 | 1/1991 | Orejola . |
| 5,016,640 | 5/1991 | Ruiz . |
| 5,053,023 | 10/1991 | Martin . |
| 5,156,592 | 10/1992 | Martin et al. . |
| 5,171,216 | 12/1992 | Dasse et al. . |
| 5,197,951 | 3/1993 | Mahurkar . |
| 5,221,255 | 6/1993 | Mahurkar et al. . |
| 5,221,256 | 6/1993 | Mahurkar . |

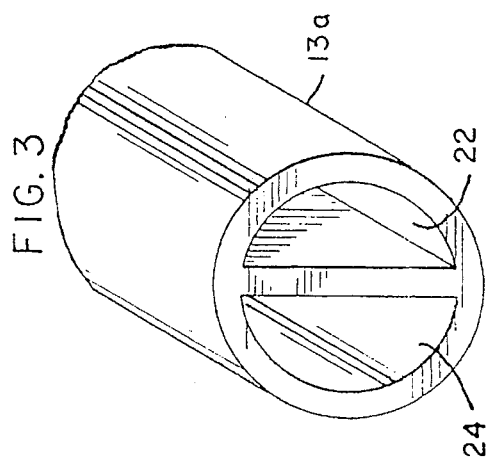
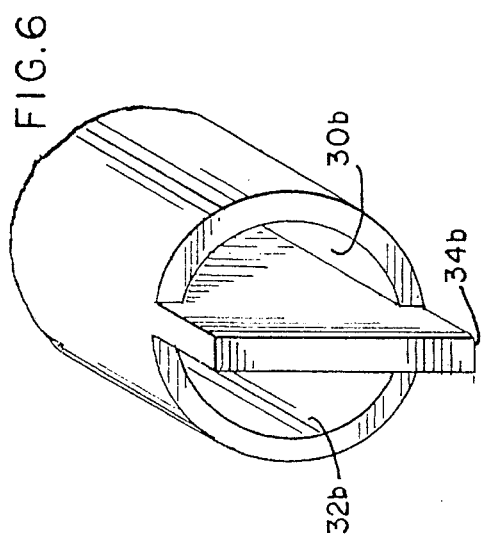
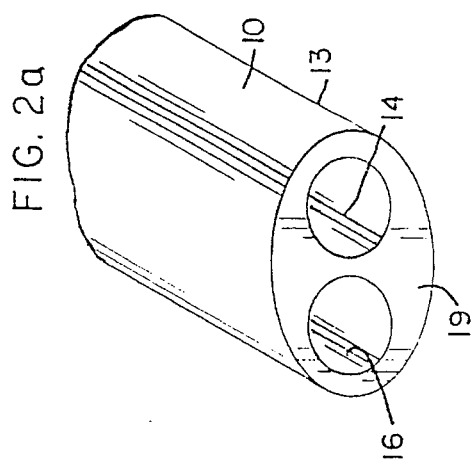
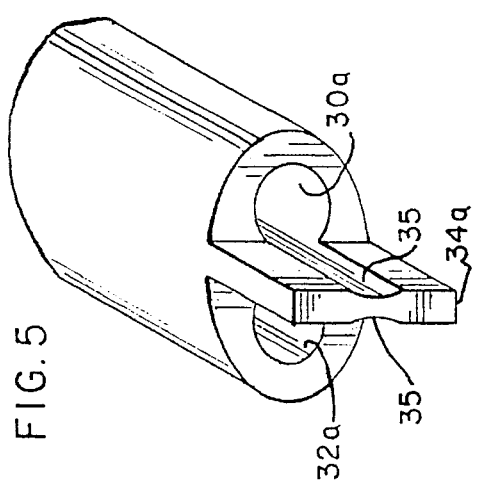
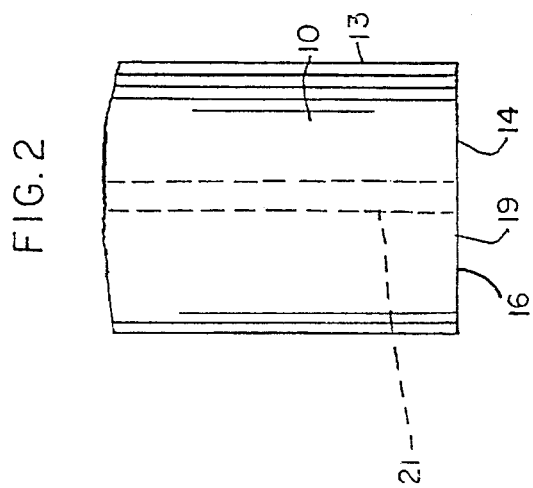
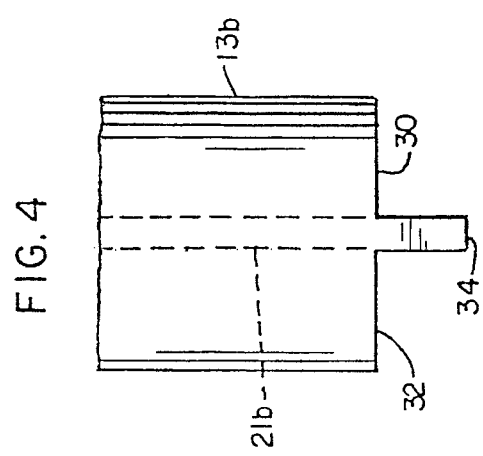

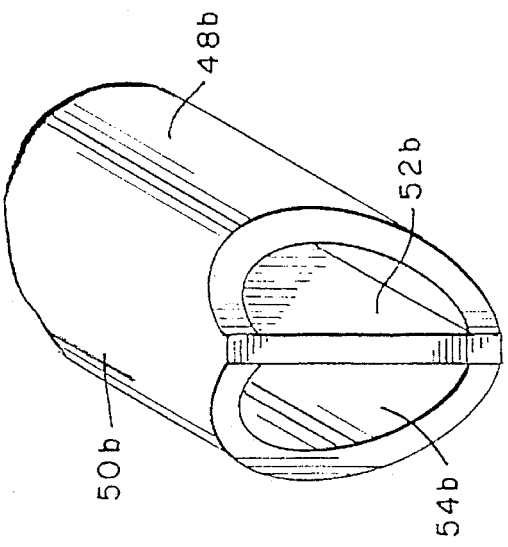
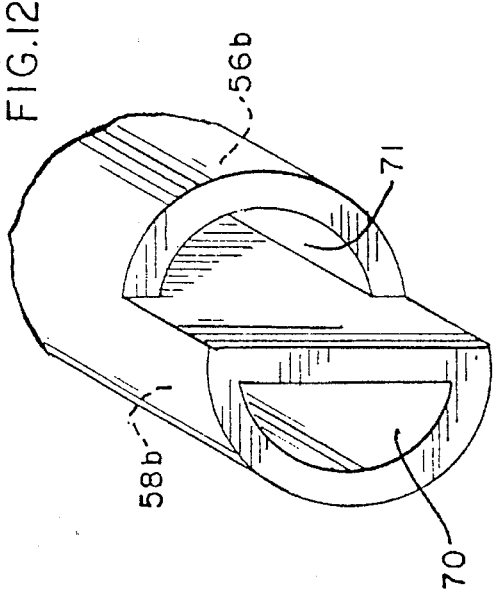
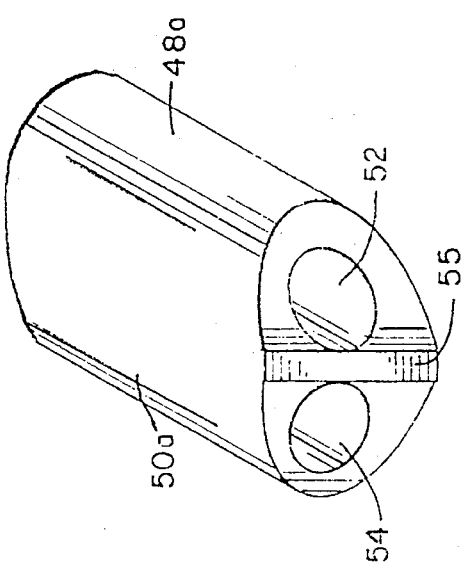
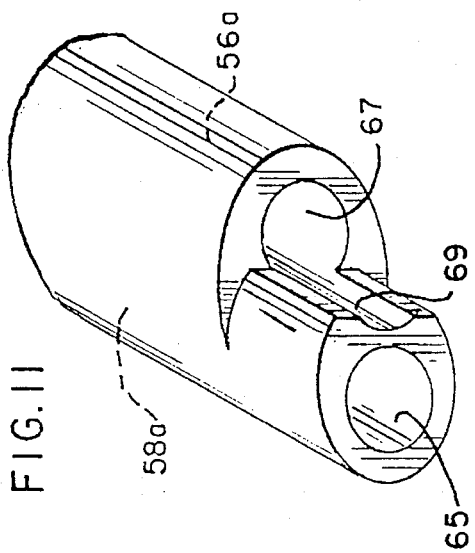
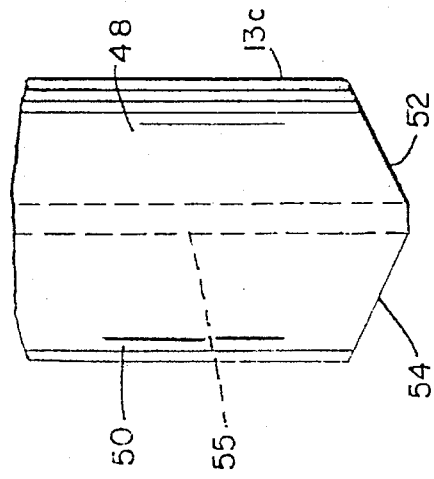
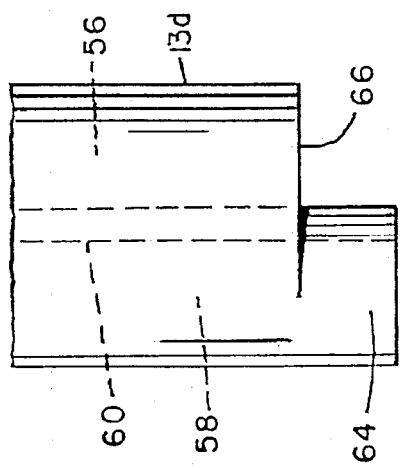

CLOT RESISTANT MULTIPLE LUMEN CATHETER AND METHOD

CROSS REFERENCE TO RELATED APPLICATION

This is a Continuation-in-Part of U.S. patent application Ser. No. 08/045,016, filed Apr. 8, 1993, now U.S. Pat. No. 5,405,320 which, in turn, is a continuation-in-part of patent application Ser. No. 07/772,613, filed Oct. 8, 1991, now U.S. Pat. No. 5,209,723; which is a continuation of application Ser. No. 07/461,684, filed Jan. 8, 1990, now abandoned.

BACKGROUND OF THE INVENTION

Multiple lumen catheters are in clinical use as blood access devices for easy and safe connection to hemodialyzers, or other blood treatment devices. Their use is desirable for chronic medical conditions, where frequent treatment of the blood of a patient is required, requiring frequent access to the vascular system.

Such catheters have a distal end which is implanted typically in a vein of the patient, while the proximal end of the catheter, when in use, communicates with a tubular set or the like which permits the circulation of blood from the vein, through the catheter, and through the set to a blood processing device such as a hemodialyzer. Then, the blood moves through typically another tubular set back to another lumen of the catheter, and then back to the vein of the patient.

Jugular and subclavian multiple lumen catheters are typically intended as permanent blood access devices. Femoral catheters are typically used as an intermediate-term blood access devices, which are expected to be removed after a period of time.

In the clinically used double lumen catheters for hemodialysis, the lumen for outflow of blood back into the vein terminates approximately 20–30 mm. beyond the lumen for inflow, which draws in blood. The purpose of this is to prevent direct recirculation of blood, which is when blood returned by one catheter lumen flows directly into the other catheter lumen again. This, of course, reduces the efficiency of the blood treatment process. This is the case for the catheters which are clinically used, and also are illustrated in Mahurkar U.S. Pat. Nos. 4,895,561; Martin 5,156,592; and Twardowski et al. 5,209,723.

Other multiple lumen catheters have flush ends in which the distal ends of the lumens terminate at the same longitudinal position along the catheter, such as in Sisley et al. U.S. Pat. No. 4,405,313. However, these catheters are not used for the withdrawing and reintroducing of large amounts of blood of a patient as is done in hemodialysis. Rather, such catheters are for the infusion of medications and/or parenteral nutrition, with only the occasional withdrawal of a sample of blood. Thus, the issue of direct blood recirculation is not a problem, and there distal end thus is designed without regard to solution of the blood recirculation problem.

The catheters for hemodialysis require high blood flows of typically 200 ml per/min or more for efficient dialysis. The direct recirculation of blood as defined above causes a reduction in the effective blood flow and thus decreases the efficiency of dialysis. Essentially, each percent of blood recirculation that is present in a catheter decreases the effective blood flow by the same one percent, which, of course, reduces the efficiency of dialysis.

In multiple lumen catheters, direct blood recirculation values of less than 15 percent are generally deemed acceptable. To achieve this, in the prior art it was believed to be mandatory to longitudinally space the distal ends of the inlet catheter lumen and the outlet catheter lumen by about 20–30 millimeters in order to avoid unduly high direct recirculation. However, several disadvantages have been noted by such large longitudinal spacings between the distal ends of the respective lumens. For example, it may be desired to reverse the blood flow through the lumens because the usual inflow lumen is not delivering sufficient blood flow due to clotting. The only other alternative is to remove the catheter. In this circumstance, the widely spaced lumen ends do not work well in that and recirculation values rise to undesirable levels. Also, it has been found that blood clots can and do attach immediately distal to the inflow lumen when there is a wide longitudinal spacing between the two distal ends of the catheter lumens.

DESCRIPTION OF THE INVENTION

By this invention, a method is provided of circulating blood through a multiple lumen catheter which connects between the vein of a patient and a blood treatment device. The lumens of the catheter each define distal ends positioned within the vein.

In accordance with this invention, one withdraws blood from the vein through one of the lumens at a flow rate of at least about 200 ml/min, while inserting blood into the vein through another of said lumens at a similar flow rate, while the distal ends of the lumens are longitudinally spaced from each other by no more than about 5 millimeters.

The blood flow rate is preferably at least about 300 ml/min. Preferably, the distal ends of the lumens are positioned beside each other without longitudinal spacing, although one lumen, preferably the outflow lumen, may extend beyond the inflow lumen by a distance of no more than about 5 mm.

In another embodiment, the lumens may be separated by a wall which projects distally beyond the lumen distal ends. This wall may comprise an extension of a septum that extends through the catheter and separates the lumens along the catheter length.

Likewise, the distal lumen ends may cause the circulating blood to pass through the ends in opposite directions, which directions diverge in acute angle relation from each other.

In the prior art, double lumen catheters that are used for hemodialysis have one lumen that projects distally by about 20–30 millimeters farther than the other lumen. The farther projecting lumen is typically the blood outflow lumen, while the other lumen is typically the blood inflow lumen. For the purposes below, "poorly functioning catheters" are defined to be multiple lumen catheters implanted in the patient having materially reduced flow due to obstruction caused by clotting. "Well-functioning catheters" are defined to be catheters that are implanted in a patient and have the expected blood flow characteristics because they are substantially free from clotting.

Recirculation studies show direct recirculation values close to zero with standard multilumen dialysis catheters having 20–30 mm lumen end spacing (inflow lumen used for inflow and the outflow lumen used for outflow) and zero to 13 percent with reversed flow (outflow lumen used for inflow and the inflow lumen used for outflow), of poorly functional catheters. (1. Moss AH, McLaughlin MM, Lempert KD, Holley JL: Use of the Silicone Catheter with a Dacron Cuff for Dialysis Short-Term Vascular Access. AM J Kidney Dis 1988;12:492–498. 2.Moss AH, Vasilakis C, Holley JL, Foulks CJ, Pillai K, McDowell DE: Use of a Silicone Dual-lumen Catheter with a Dacron cuff as a Long-term Vascular Access for Hemodialysis Patients. Am. J. Kidney Dis. 1990; 16:211–215).

Our own study (Twardowski ZJ, Van Stone JC, Jones ME, Klusmeyer MS Haynie JD: Blood Recirculation in Intravenous Catheters for Hemodialysis. JASN 1993; 3: 1978–1981) shows that the direct recirculation values of well-functioning conventional catheters as before, with standard lumen flow directions, were close to zero at 300 ml/min blood flow and similar to those already reported. Recirculation values of poorly functional catheters with reversed flows through the lumens were higher than those with standard lumen flow but not exceeding 15%. However, recirculation values with reversed flow and well-functioning catheters were much higher (up to 40%), exceeding those with reversed flow, poorly functioning catheters.

This represents a significant inefficiency of blood transport which will result in inefficient dialysis. We speculated that the poorly functional catheters contain a clot at the inflow lumen. These clots blocked the outlet of blood to the catheter, and caused its dispersion and mixing with the blood flowing back into the vein. The survival probability of poorly functioning catheters is markedly reduced, but they may function several months, and are frequently used until they completely fail.

Well-functioning catheters do not contain any obstacle to the outflowing blood stream with reversed lumens. Laminar flow of this blood stream along the catheter wall is believed to cause its free passage by the inflow lumen, thus allowing its suction into the inflow blood lumen.

This study prompted us to propose that the distance between inflow and outflow tubing might be markedly shortened to 5 mm or less without a risk of undue recirculation. We further propose that the shortening of the outflow tubing beyond the inflow lumen end can decrease the clot retention on the outflow tubing, and thus improve the function of the catheter. An experience with fourteen such catheters confirmed our predictions, and showed that the flow problems with such catheters are significantly less. As predicted, direct recirculation values at 300 ml/min with double lumen catheters that have distal lumen ends longitudinally spaced by about 5 mm., using the standard flow direction, were close to zero (Mean±SD) (1.59%±4.35%). Moreover, the recirculation values at 300 ml/min with reversed flow in such well-functioning, double lumen catheters turned out to be less than the values for catheters where the distance between lumens was 20–30 mm (Mean±SD) (4.17%±7.34%).

Further, catheters with flush inflow and outflow lumen bores side-by-side tend to not exhibit high direct recirculation at higher blood flows.

We made prototypes of such catheters with flush inflow and outflow lumen bores (zero longitudinal spacing of the distal lumen ends). The catheter was implanted through the right internal jugular vein into the right atrium. Arbitrarily one blood flow direction was called "standard", and the opposite direction was called "reversed." Measurements of direct recirculation in three such catheters shows the following direct recirculation values in percent:

| Flow (ml/min) | Flow direction | Mean | Standard Deviation | Flow direction | Mean | Standard Deviation |
| --- | --- | --- | --- | --- | --- | --- |
| 100 | Standard | 21.5 | 2.4 | Reversed | 14.8 | 1.6 |
| 300 | Standard | 9.3 | 1.4 | Reversed | 6.5 | 1.4 |
| 500 | Standard | 8.7 | 1.9 | Reversed | 10.7 | 1.8 |

Direct recirculation at low blood flow (100 ml/min) can be seen to be higher than the same at high blood flows (300 and 500 ml/min). Apparently, at low flow rate, the velocity of the stream is insufficient to prevent outflowing blood from being sucked into the inflow lumen. Thus, normal flow direct recirculation values of catheters having flush lumen ends are similar to catheters having lumen ends spaced by 20–30 mm with standard flows at high blood flows. However, the direct recirculation values of the reversed flow catheters of this invention are lower than similar reversed flow catheters with 20–30 mm spacing of between inflow and outflow lumen distal ends. The catheter of this invention thus provides sufficient blood flow with acceptable low recirculation in either flow direction, contrary to those of the prior art.

There are two major advantages with the catheter of this invention:

1. The recirculation is similar in either direction of the blood flow.
2. The probability of blood clot attachment at or immediately distal to the inflow lumen is less likely because there is little or no support for such an attachment. Consequently, such a catheter will provide good flow, fewer clotting problems, and longer survival.

In this invention, the typical catheters for long-term hemodialysis access are intended to be inserted into the superior vena cava or right atrium through one of the following veins:

1. Right internal jugular vein
2. Left internal jugular vein
3. Right subclavian vein
4. Left subclavian vein For intermediate-term blood access, the catheter may be inserted into the common iliac vein or inferior vena cava through a femoral vein. The overall design of the catheters may be similar to those in U.S. Pat. No. 5,209,723, except as otherwise disclosed herein.

In one embodiment of the invention, the catheter inflow and outflow bores are flush, but separated by a small septum typically extending about 1–5 mm beyond the lumen bores. Such a septum decreases blood recirculation. In these embodiments, the direction of blood flow through the catheter lumens does not strongly affect blood recirculation. Also, a small-sized septum is unfavorable for the firm anchoring of the clot. Small clots attached to the septum may be washed away by alternating flow directions with consecutive dialyses. The lumen bores may be slightly angled at their distal ends.

In yet another embodiment of the invention, the catheter outflow bore extends beyond the inflow bore by no more than 1–5 mm. Such a configuration provides recirculation values close to zero with standard flow, and minimal (less than those with conventional tip configuration) recirculation with reversed flow. Such a small-sized outflow lumen extension is unfavorable for the firm anchoring of clots.

DESCRIPTION OF THE DRAWINGS

In the drawings.

FIG. 2 is an enlarged, plan view of one embodiment of the distal tip of the catheter in accordance with this invention;

FIG. 2a is a perspective view of the distal tip of FIG. 2a;

FIG. 3 is a perspective view of the distal tip of a modified catheter of FIG. 2;

FIG. 4 is an enlarged, plan view of the distal tip of another embodiment of catheter in accordance with this invention;

FIGS. 5 and 6 are perspective views of different embodiments of catheter distal tips similar to that of FIG. 4;

FIG. 7 is an enlarged, plan view of another embodiment of the distal tip of the catheter of this invention;

FIG. 8 is a perspective view of the distal tip shown in FIG. 7;

FIG. 9 is a perspective view of another embodiment of catheter as shown in FIG. 7;

FIG. 10 is an enlarged, plan view of another embodiment of catheter distal tip in accordance with this invention;

FIG. 11 is a perspective view of the catheter distal tip of FIG. 10; and

FIG. 12 is another embodiment of catheter distal tip of the type shown in FIG. 10.

DESCRIPTION OF SPECIFIC EMBODIMENTS

Figure 1:
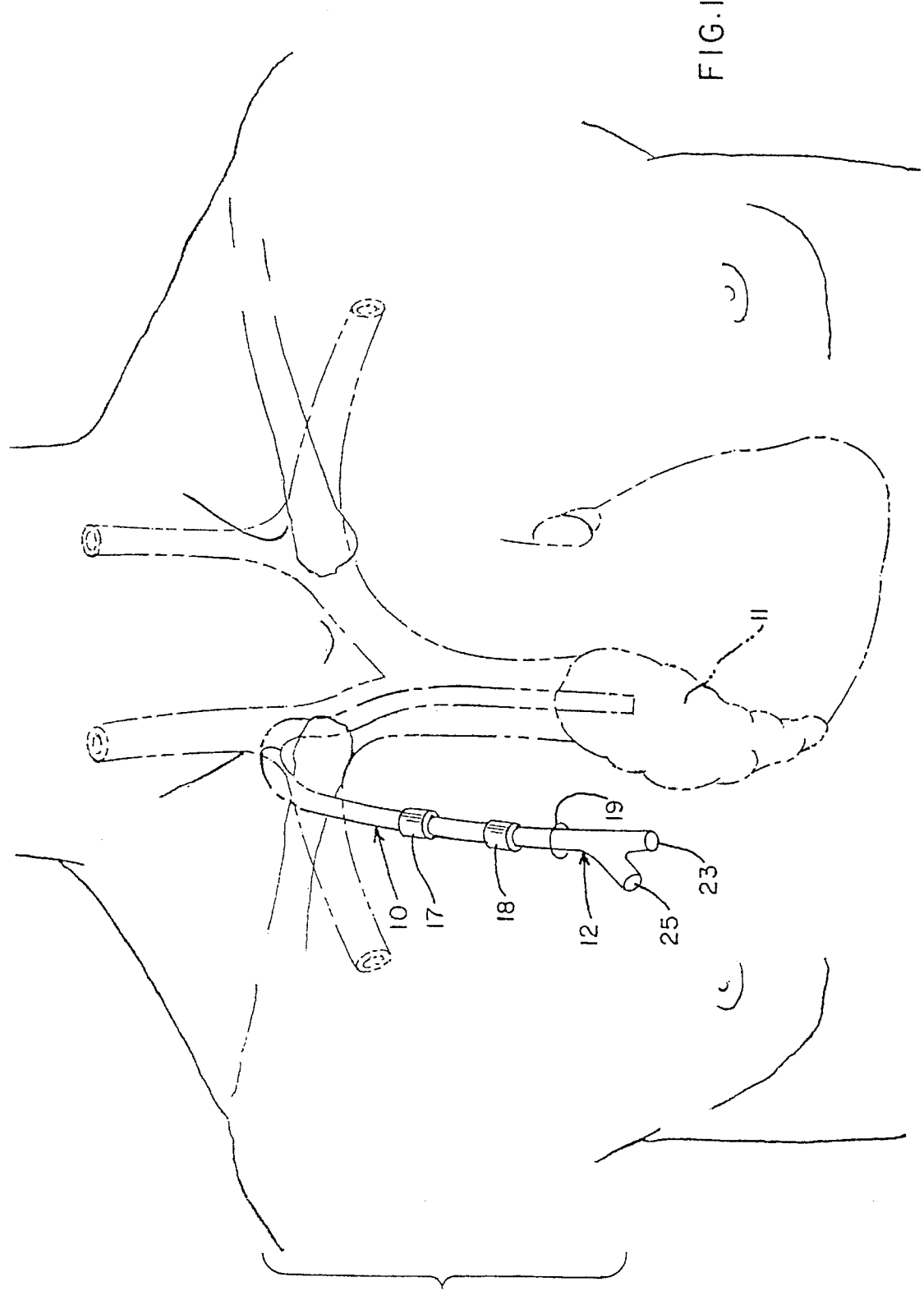
FIG. 1 is a perspective view of a double lumen dialysis catheter, shown to be implanted intravenous system of a patient.

Referring to FIG. 1, a catheter 10 in accordance with this invention is shown implanted in the right atrium 11 of the heart through the right jugular vein of a patient. The implantation is intended to be permanent, with the result that the patient can be freed from the burden of needle "sticks" three times a week or so with a pair of fistula needles. Rather, the catheter 10 can be simply connected and disconnected to dialysis sets through a Y-connector 12, each branch of which communicates with one of lumens 14, 16, which are shown in FIGS. 2–12, for example.

The overall design of catheter 10 may be conventional, and may be of any of the embodiments described in the allowed application of Zbylut J. Twardowski, Ser. No. 08/045,016, filed Apr. 8, 1993, now U.S. Pat. No. 5,405,320. Also, catheter 10 may be implanted in other positions of the body, as desired.

Catheter 10 is shown to be implanted in its natural, unstressed shape, which corresponds in the distal section of the catheter with the shape of the vein or veins in which catheter 10 resides. Such catheters exhibit less pressure and abrasion against the blood vessel walls, resulting in a reduction in blood clotting and tissue irritation.

Catheter 10 also has a pair of conventional tissue adhering cuffs, 17, 18, for permanent implantation of the catheter in the patient as is shown. The distal end of catheter 10, carrying Y site 12, then projects outwardly from an incision site 19 through the skin.

The distal end of catheter 10 extends, as previously stated, into the right atrium 11 of the heart, although such positioning is merely preferable and not essential to the invention.

The remaining FIGS. 2–12 pertain to differing designs of catheter, particularly with reference to the design of the catheter distal end 13. Any of the designs disclosed may be used with any type of catheter of any desired overall shape, particularly those previously described in the patents cited above and the prior allowed application Ser. No. 08/045,016.

FIGS. 2 and 2a show a tip 13 of catheter 10 which comprises a basically flat catheter end 19 which, if desired, may be slightly convex if not flat. Catheter 10 is a double lumen catheter having lumens 14, 16 and may be in generally oval cross-section is shown in FIG. 2a. The respective lumens, 14, 16 are separated by a septum 21 that extends substantially the entire length of the catheter, so that lumen 14 can communicate with tubular branch 23 of the Y-connector, and tubular 16 can connect with the tubular branch 25, for separate flow communication. Lumens 14, 16 each typically have a diameter of at least 2 mm.

Thus, blood can flow from a set connected to one of the branches of Y-connector 12, preferably at a flow rate of at least about 200 ml/min. Blood is then simultaneously withdrawn through the other lumen of the catheter and passes through the other tubular branch of the Y-connector 12, so that a constant stream of blood may be provided to a dialysis system or the like and then returned to the patient.

It is believed that because of the relatively high velocity of the blood, little direct recirculation of blood flow is encountered between the blood pouring into the atrium 12 from lumen 14 and the blood which is being taken up again through lumen 16.

Referring to FIG. 3, a modified embodiment 13a of the catheter tip is shown, with the remainder of the catheter being typically of similar design. As before, a pair of lumens 22, 24 are provided in a manner similar to lumens 14, 16 in the preceding embodiment. The tip of this catheter is flat in its cross-section, similar to the previous embodiment.

Referring to FIG. 4, another embodiment 13b of catheter tip is shown having double lumens 30, 32, which end flush with each other as shown. However, in this embodiment, septum 34 extends about 1–5 mm (typically 3 mm) beyond the ends of lumens 30, 32. Such a short septum 34 provides improvements in the reduction of immediate blood recirculation from one lumen to the other, while at the same time, the septum extension 34 is too short to support a significant amount of blood clotting. It can be seen that septum 34 comprises an extension of the internal septum 21b found in this and most double lumen catheters.

FIG. 5 shows a perspective view of one embodiment of the catheter tip of FIG. 4. Lumens 30a, 32a are separated by a septum 34a which has a cylindrical recess 35 on each side thereof to facilitate blood inflow and outflow from the lumens 30a, 32a.

Referring to FIG. 6, another perspective view of a catheter distal end is shown, being another possible embodiment of the catheter tip of FIG. 4. The catheter tip in this embodiment is round in cross-section with lumens 30b, 32b assuming a D-shaped cross-section and a greater height. Also, septum 34b is of the shape of a flat plate, without the recesses of the previous embodiment. Septum 34b also extends about 1–5 mm beyond the lumen bores, for example, 4 mm, and represents an extension of the internal septum that extends the length of the catheters disclosed herein.

Referring to FIG. 7, a catheter tip 13c is shown, comprising the two lumens 48, 50, similar to previous embodiments, with lumens 48, 50 being separated by septum 55 in a manner also similar to the previous embodiments. In this embodiment, the distal tip face comprises lumen ends which, in cross-section, comprise flat faces 52, 54 which are in an obtuse angle relation to each other, preferably an angle to each other of 100°–170° so that each face is angled at about 10°–45° to a plane perpendicular to the longitudinal axis of the catheter.

Referring to FIG. 8, one embodiment of FIG. 7 is shown in which lumens 48*a*, 50*a* terminate in angled relationship as shown.

Referring to FIG. 9, a catheter of different cross-sectional shape is shown, resulting in different cross-sectional shapes for lumens 48*b*, 50*b* and their end faces 52*b*, 54*b*.

It can be seen that, in the catheters of the previous embodiments, it is substantially immaterial which of the lumens is the inflow lumen and which of the lumens is the outflow lumen since the catheters are symmetrical. Referring, however, to FIG. 10, asymmetrical catheter designs are shown which can provide advantageous blood flow characteristics with low direct blood recirculation and low long-term clotting at the catheter distal tips.

FIG. 10 shows a catheter tip 13*d* which has a pair of lumens 56, 58 separated by a septum 60, in which the distal end of 64 of lumen 58 extends about 1–5 mm beyond the distal end 66 of lumen 56, for example, 5 mm. In this embodiment it is generally advantageous for lumen 58 to be the blood outflow lumen, while lumen 56 is the blood inflow lumen, taking blood into the catheter for conveyance and processing in a dialyzer for the like. However, good results are achieved with reverse flow at 200 ml./min. or more.

As shown in FIG. 11, the extension 65 of lumen 58*a* beyond the end 67 of lumen 56*a* may define a side groove 69. which is basically a cylindrical section, to facilitate blood flow either into or out of lumen 56*a*. In this embodiment, lumens 56*a*, 58*a* are seen to be round in cross-section.

However, in FIG. 12, a similar overall structure is shown as another embodiment of FIG. 10, in which the lumens 56*b*, 58*b* and their respective ends 64*b*, 66*b* are in the same relationship as shown in FIGS. 10 and 11, but due to the cross-sectional dimensions of the catheter, the lumens are D-shaped, as shown.

Here, it is generally preferred for the outflow lumen to be lumen 58, 58*a*, or 58*b* while the inflow lumen is lumen 56, 56*a*, or 56*b*. Because the lumen ends 65, 70 extend no more than about 5 mm beyond the ends 66, 67, 71 of lumens 56, 56*a*, 56*b*, the catheters of this design have reduced, clinically disadvantageous direct blood recirculation. The above designs also suppress clot formation at the catheter distal tip.

The above has been offered for illustrative purposes only, and is not intended to limit the scope of the invention of this application, which is as defined in the claims below.

That which is claimed is:

1. The method of circulating blood through a multiple lumen catheter which extends in substantially an inverted U-shape in the patient and connects between a vein of a patient and a blood treatment device, said catheter and the lumens thereof each defining blunt, distal ends positioned within said vein, comprising the steps of:

withdrawing blood from said vein through one of said lumens at a flow rate of at least about 200 mi./min.; and inserting blood into said vein through another of said lumens at a similar flow; the distal ends of said lumens being longitudinally spaced from each other by no more than about 5 mm.

2. The method of claim 1 in which the circulating blood passes through said distal lumen ends in substantially parallel but opposite directions.

3. The method of claim 1 in which said flow rate is at least about 300 mi./min.

4. The method of claim 1 in which said distal ends of the lumens are positioned beside each other without longitudinal spacing.

5. The method of claim 4 in which the distal ends of said lumens are separated by a wall projecting distally beyond said lumen distal ends.

6. The method of claim 5 in which said wall comprises an extension of a septum that extends through said catheter and separates said lumens along the catheter length.

7. The method of claim 1 in which the circulating blood passes through distal lumen ends in opposite directions, which directions diverge in acute angle relation from each other.

8. The method of claim 1 in which said method is repeated intermittently, using a catheter which is permanently implanted in the patient.

9. The method of repeatedly and intermittently circulating blood through a permanently implanted, multiple lumen catheter which extends in substantially an inverted U-shape in the patient and connects between a vein of a patient and a blood treatment device, said catheter and the lumens thereof each defining soft, blunt distal ends positioned within said vein, comprising the steps of withdrawing blood from said vein through one of said lumens at a flow rate of at least 300 ml/min.; and inserting blood into said vein through another of said lumens at a similar flow in a substantially parallel but opposite direction to the flow direction of withdrawing blood; the distal ends of said lumens being longitudinally spaced from each other by no more than about 5 mm.

10. The method of claim 9 in which said distal ends of the lumens are positioned beside each other without longitudinal spacing.

* * * * *